(12) United States Patent
Akagane

(10) Patent No.: US 10,966,745 B2
(45) Date of Patent: Apr. 6, 2021

(54) MEDICAL DEVICE

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 392 days.

(21) Appl. No.: 15/855,253

(22) Filed: Dec. 27, 2017

(65) Prior Publication Data

US 2018/0116688 A1    May 3, 2018

Related U.S. Application Data

(63) Continuation of application No. PCT/JP2016/063886, filed on May 10, 2016.

(30) Foreign Application Priority Data

Jun. 30, 2015   (JP) .............................. JP2015-131294

(51) Int. Cl.
  *A61B 17/32*   (2006.01)
  *A61B 18/14*   (2006.01)
  *A61B 18/00*   (2006.01)

(52) U.S. Cl.
  CPC .. *A61B 17/320092* (2013.01); *A61B 18/1445* (2013.01); *A61B 2017/32009* (2017.08); *A61B 2017/320072* (2013.01); *A61B 2017/320073* (2017.08); *A61B 2017/320093* (2017.08); *A61B 2017/320094* (2017.08);
(Continued)

(58) Field of Classification Search
  CPC ........ A61B 17/320092; A61B 18/1445; A61B 2017/320072; A61B 2017/320073; A61B 2017/32009; A61B 2017/320093; A61B 2017/320094; A61B 2017/320095; A61B 2018/00083; A61B 2018/00101;
(Continued)

(56) References Cited

U.S. PATENT DOCUMENTS

| 6,129,735 A * | 10/2000 | Okada ............ A61B 17/320068 606/169 |
| 2009/0143806 A1 * | 6/2009 | Witt ........................ A61N 7/00 606/169 |
| 2014/0135804 A1 * | 5/2014 | Weisenburgh, II .... A61B 17/29 606/169 |

FOREIGN PATENT DOCUMENTS

| JP | H11-128238 A | 5/1999 |
| JP | H11-508171 A | 7/1999 |

(Continued)

OTHER PUBLICATIONS

Mar. 28, 2017 Office Action issued in Japanese Patent Application No. 2017-501428.
(Continued)

*Primary Examiner* — Katherine M Shi
(74) *Attorney, Agent, or Firm* — Oliff PLC

(57) ABSTRACT

A medical device according to one embodiment of the present invention includes: a vibration transmission member that comprises a node position of vibration and an area including the node position and a portion at a distal end side relative to the node position, and to which the vibration is transmitted; a first coating that covers a side of the node position of the area; and a second coating that covers a distal end side relative to the first coating of the area and has a thickness smaller than that of the first coating.

17 Claims, 4 Drawing Sheets

(52) U.S. Cl.
CPC ............ *A61B 2017/320095* (2017.08); *A61B 2018/00083* (2013.01); *A61B 2018/00101* (2013.01); *A61B 2018/00607* (2013.01); *A61B 2018/00994* (2013.01); *A61B 2018/1455* (2013.01)

(58) Field of Classification Search
CPC ........... A61B 2018/00607; A61B 2018/00994; A61B 2018/1455
See application file for complete search history.

(56) References Cited

FOREIGN PATENT DOCUMENTS

| | | |
|---|---|---|
| JP | 2011-505198 A | 2/2011 |
| WO | 2015/020147 A1 | 2/2015 |

OTHER PUBLICATIONS

Aug. 9, 2016 International Search Report issued in International Patent Application No. PCT/JP2016/063886.
Jan. 2, 2018 International Preliminary Report on Patentability issued in Patent Application No. PCT/JP2016/063886.
Dec. 4, 2019 Office Action issued in Chinese Patent Application No. 201680037836.6.

\* cited by examiner

MEDICAL DEVICE

CROSS-REFERENCE TO RELATED APPLICATIONS

This application is a Continuation Application of PCT Application No. PCT/JP2016/063886, filed May 10, 2016 and based upon and claiming the benefit of priority from Japanese Patent Application No. 2015-131294, filed Jun. 30, 2015, the entire contents of which are incorporated herein by reference.

BACKGROUND OF THE INVENTION

1. Field of the Invention

The present invention relates to a medical device that treats living tissue by energy such as ultrasonic vibration.

2. Description of the Related Art

Jpn. PCT National Publication No. 2011-505198 discloses an ultrasonic surgical blade as a minimally invasive surgical tool. The ultrasonic surgical blade uses an ultrasonic transducer to generate mechanical vibration by ultrasonic frequencies and transmit the mechanical vibration to an end effector via a transmitting element. By a vibration motion of the end effector, heat is generated in the tissue to incise and coagulate the tissue.

BRIEF SUMMARY OF THE INVENTION

A medical device according to one embodiment of the present invention includes: a vibration transmission member that comprises a node position of vibration and an area including the node position and a portion at a distal end side relative to the node position, and to which the vibration is transmitted; a first coating that covers a side of the node position of the area; and a second coating that covers a distal end side relative to the first coating of the area and has a thickness smaller than that of the first coating.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

First Embodiment

The first embodiment of the medical device of the present invention will be described with reference to FIGS. 1 to 4. The medical device is a treatment tool that applies various energies to living tissue of a treatment target to perform various treatments such as incision, excision, coagulation, and blood stanching.

Figure 1:
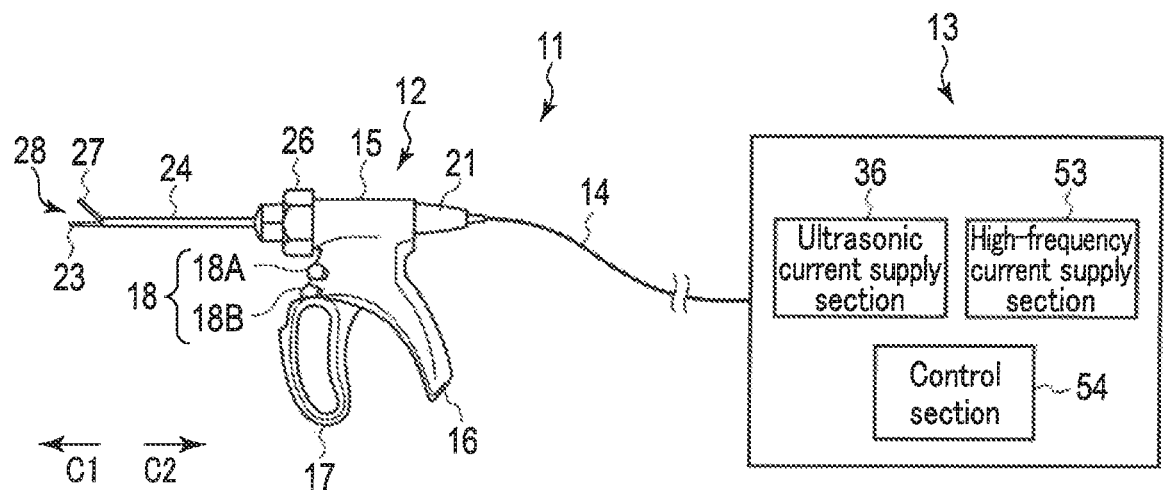
FIG. 1 is a schematic view showing an entire configuration of a medical device according to a first embodiment.

As shown in FIG. 1, a medical device 11 includes a hand piece 12, a power supply unit 13, and a cable 14 connecting the hand piece 12 and the power supply unit 13.

Figure 4:
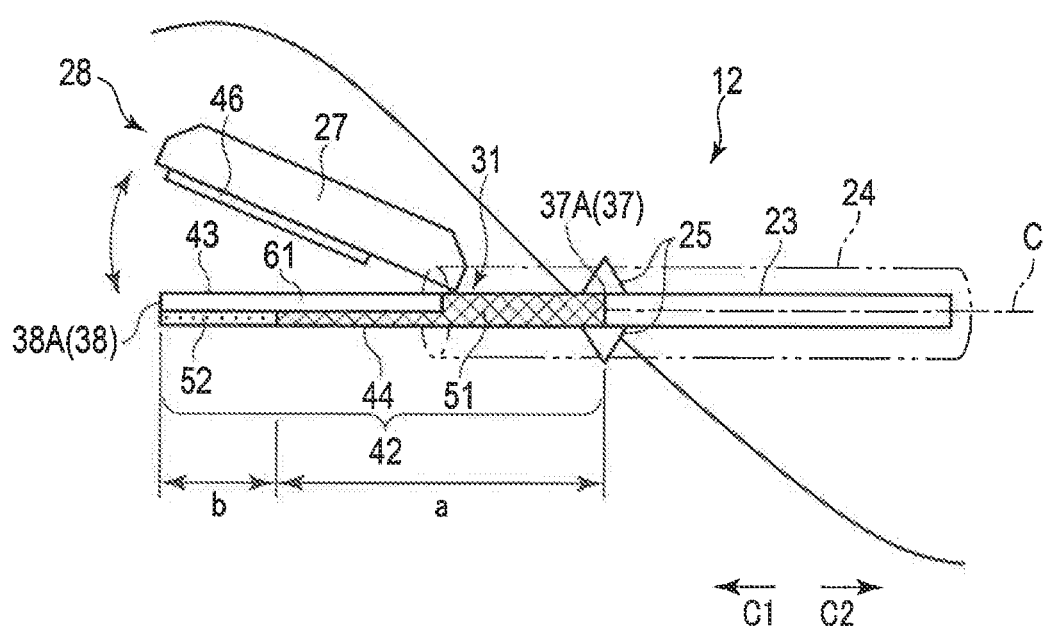
FIG. 4 is a side view showing the vibration transmission member shown in FIG. 1, the jaw, the first and second coatings of a coating portion, and a waveform at the moment when the ultrasonic vibration transmitted to the vibration transmission member is at maximum amplitude.

As shown in FIGS. 1 and 4, the hand piece 12 includes a housing 15 forming an outer shell, a fixed handle 16 provided integral with the housing 15, a handle 17 (movable handle) rotatable with respect to the housing 15, a plurality of operation buttons 18 provided in the housing 15, a vibration generation section 22 (transducer) contained in a case 21 that is detachable to the housing 15, a rod-shaped vibration transmission member 23 (probe) connected to the vibration generation section 22, a cylindrical sheath 24 (tubed-shaped member) covering the periphery of the vibration transmission member 23 to protect the vibration transmission member 23, a ring-shaped supporting section 25 (lining) provided between the vibration transmission member 23 and the sheath 24, a knob 26 (rotating knob) fixed to the sheath 24, a jaw 27 attached to the distal end of the sheath 24 and rotatable with respect to the sheath 24, a cylindrical movable pipe provided inside the sheath 24 and advanced or retreated when the jaw 27 opens and closes, an end effector 28 provided at the distal end side of the vibration transmission member 23, and a coating portion 31 covering a part of the vibration transmission member 23. In this embodiment, one of two directions parallel to a longitudinal direction (central axis direction) C of the vibration transmission member 23 is referred to as a distal direction C1, and a direction opposite to the distal direction C1 is referred to as a proximal direction C2.

Figure 3:
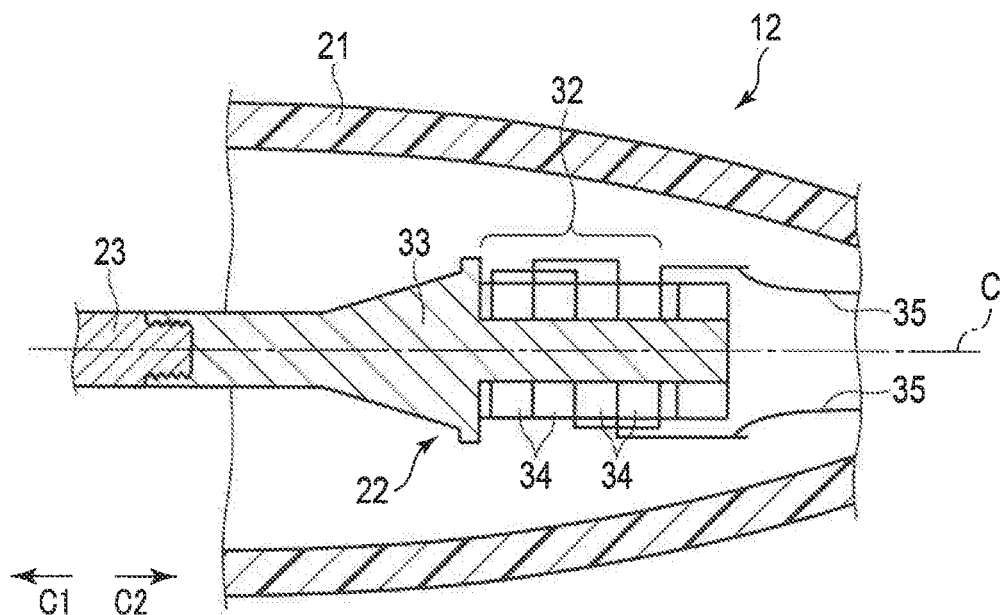
FIG. 3 is a cross-sectional view showing a vibration generation section of the medical device shown in FIG. 1.

As shown in FIG. 3, the vibration generation section 22 includes an ultrasonic vibrator 32 and a horn member 33. The ultrasonic transducer 32 is provided with a plurality of piezoelectric elements 34 (four piezoelectric elements in the present embodiment) for changing a current into ultrasonic vibration. The ultrasonic transducer 32 is connected to one end of an electrical line 35. The electrical line 35 extends inside the cable 14 and connects with an ultrasonic current supply section 36 of the power supply unit 13 at the other end. When power is supplied from the ultrasonic current supply section 36 to the ultrasonic vibrator 32 through the electrical line 35, the ultrasonic vibrator 32 generates ultrasonic vibrations. Accordingly, the vibration generation section 22 forms a supply source of vibration in the hand piece 12.

As shown in FIG. 3, the ultrasonic transducer 32 is attached to the horn member 33. The horn member 33 is made of a metallic material. The horn member 33 is provided with an approximately cone-shaped cross-section transition portion, whose cross-sectional area decreases in the distal direction C1 of the vibration transmission member 23. Regarding the ultrasonic vibration generated by the ultrasonic transducer 32, the cross-section transition portion increases the amplitude of the ultrasonic vibration.

As shown in FIG. 4, the supporting section 25 is provided at a node position 37 of the ultrasonic vibration generated by the vibration generation section 22 (in the figure, the waveform at the moment when the amplitude is at maximum is shown by the sine curve-like line). The supporting section 25 is formed by a resin material and has rubber-like elasticity. The supporting section 25 supports the vibration transmission member 23 and seals the inside of the sheath 24 so that liquids or treatment pieces of the living tissues do not enter the proximal direction C2 side relative to the supporting section 25.

Figure 2:
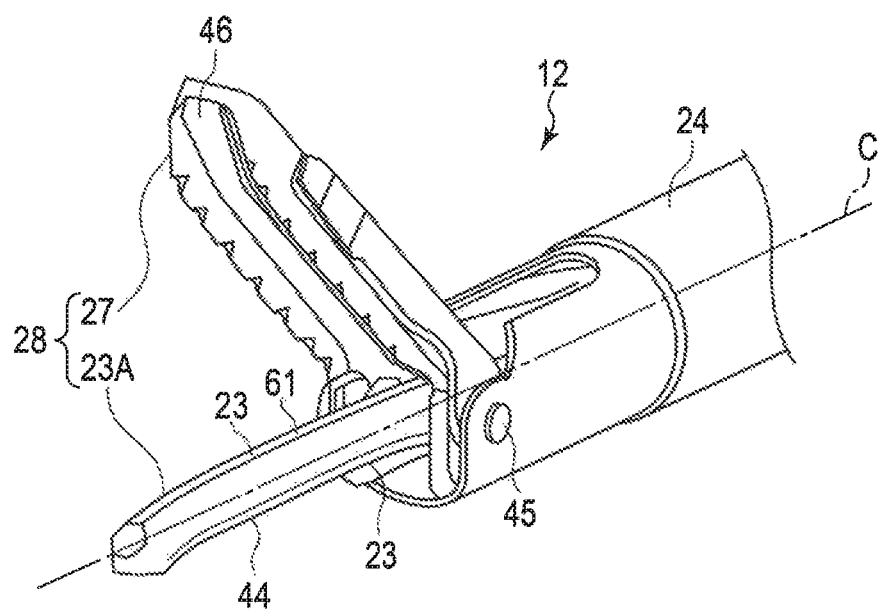
FIG. 2 is a perspective view showing a distal end of a vibration transmission member and a jaw of a hand piece of the medical device shown in FIG. 1.

As shown in FIGS. 2 and 4, the vibration transmission member 23 (probe) is formed into a rod of, for example, a biocompatible metallic material (such as titanium alloy) in which the distal direction C1 side is curved laterally. The vibration transmission member 23 includes a plurality of node positions 37 and antinode positions 38 of the ultrasonic vibration (vibration) transmitted from the vibration generation section 22, a distal node position 37A located on the most distal direction C1 side of the vibration transmission member 23 among the node positions 37, an area 42 (treatment area) including the distal node position 37A and a part at the distal direction C1 side of the vibration transmission member 23 relative to the distal node position 37A, an exposed section 61 provided on a part brought into contact with a pad 46 in the area 42, and a distal antinode position 38A corresponding to the distal end of the vibration transmission member 23 among the antinode positions 38. The length from the distal node position 37A to the distal antinode position 38A is ¼ of the wavelength of the ultrasonic vibration (vibration) transmitted to the vibration transmission member 23. The vibration transmission member 23 includes a treatment surface 43 provided on a portion opposed to the jaw 27, and a back surface 44 opposite to the treatment surface 43. The proximal end opposite to the distal end of the vibration transmission member 23 is connected to one of two second electrical lines. This one of the second electrical lines extends inside the cable 14 and connects with one output terminal of a high-frequency supply section 53 at the other end. The exposed section 61 is not covered with the coating portion 31 (the first coating 51 or the second coating 52).

That is, to the vibration transmission member 23, ultrasonic vibration is transmitted from the vibration generation section 22, and a high-frequency current is supplied from the high-frequency current supply section 53. Therefore, the vibration transmission member 23 not only applies ultrasonic vibration to living tissues but functions as one pole of a bipolar electrode for performing bipolar treatment.

As shown in FIGS. 1 and 2, the sheath 24 has a cylindrical shape and protects the vibration transmission member 23 located inside. The sheath 24 is attached to the housing 15 to be rotatable with respect to the housing 15 at the proximal end. The knob 26 is fixed to the sheath 24. By rotating the knob 26 relative to the housing 15, the knob 26, the sheath 24, the vibration transmission member 23, the ultrasonic transducer 32, and the jaw 27 are integrally rotated about the central axis C. The sheath 24 includes a supporting pin 45 for supporting the jaw 27 at the distal end. The proximal end of the sheath 24 is connected to the other one of two second electrical lines. The other one of the second electrical lines extends inside the cable 14 and connects with the other output terminal of the high-frequency current supply section 53 at the other end.

The jaw 27 is an example of a clamp member that is, as indicated by the arrow in FIG. 4, rotatable around the supporting pin 45 (refer to FIG. 2) between a contact position where the jaw 27 is brought into contact with the vibration transmission member 23 and a spaced position where the jaw 27 is spaced apart from the vibration transmission member. The jaw 27 is electrically connected to the sheath 24 via the supporting pin 45. Thus, the jaw 27 at the distal end of the sheath 24 functions as the other pole of the bipolar electrode for performing bipolar treatment. The electrode part of the jaw 27 is made of, for example, copper alloy and the like. As illustrated in FIGS. 2 and 4, the jaw 27 includes a pad 46 that is directly brought into contact with the vibration transmission member 23. The pad 46 is made of a resin material having excellent slidability such as a fluorine-based resin. The pad 46 extends to have a shape of a thin long plate along the main body of the jaw 27.

As illustrated in FIGS. 2 and 4, the end effector 28 includes a distal end 23A of the vibration transmission member 23 (first gripping piece) and the jaw 27 (second gripping piece). In treatment, the operator opens or closes the jaw 27 to operate the end effector 27 like a forceps to thereby hold the treatment target between the distal end 23A and the jaw 27. The end effector 28 applies treatment energies (ultrasonic energy and electric energy) for cauterizing or incising or both cauterizing and cutting living tissue to the treatment target (living tissue) while holding them as described above to perform treatments such as incision or coagulation on the living tissue. In the above-described embodiment, the treatment energies are ultrasonic energy and electric energy; however, any of ultrasonic energy, high-frequency energy, thermal energy, light energy, electromagnetic wave and kinetic energy may be output alone, and a suitable combination of these energies may be output.

By rotating the handle 17 with respect to the housing 15, the operator is capable of performing an open/close operation of the jaw 27. That is, when the operator operates the handle 17, a movable pipe provided inside the sheath 24 moves along the central axis C of the sheath 24, thereby, causing the jaw 27 to perform an open/close motion.

As illustrated in FIG. 4, the coating portion 31 includes a first coating 51 covering the distal node position 37A (node position) side of the area 42 (treatment area) of the vibration transmission member 23, and a second coating 52 covering the distal end side of the vibration transmission member 23 relative to the first coating 51. The coating portion 31 is made of the resin (synthetic resin) having electrical insulation properties and heat insulation properties, but may be made of materials having at least one of the electrical insulation properties and the heat insulation properties. The coating portion 31 may have water repellent properties and oil repellent properties. For the coating portion 31, resin materials such as PEEK may be used, but other types of resins may also be used. The heat insulation property described in the present specification means that thermal conductivity is sufficiently small as compared to the vibration transmission member 23 (metal) and the like.

The first coating 51 and the second coating 52 are made of the same material but have different thicknesses. The second coating 52 has a thickness smaller than that of the first coating 51. Specifically, in consideration of non-uniformity, the first coating 51 is formed to have a suitable thickness, for example, within the range of 60 to 200 μm, and the second coating 52 is formed to have a suitable thickness, for example, within the range of 1 to 60 μm. The first coating 51 and the second coating 52 are provided only on the back surface 44 of the vibration transmission member 23 at the position opposed to the jaw 27, and not provided on the treatment surface 43. On the other hand, at the portion of the first coating 51 not opposed to the jaw 27, the entire periphery of the vibration transmission member 23 is covered.

The second coating 52 is provided in the range of, for example, a length of ⅛ of the wavelength of the ultrasonic vibration (vibration) from the distal end (distal antinode position 38A) of the vibration transmission member 23. In this case, the second coating 52 is provided on any portion of a part opposed to the pad 46. In the present embodiment, the second coating 52 is provided on the entire part corresponding to the pad 46 of the jaw 27, and provided at the position overlapping with the pad 46. The second coating 52 may be provided on a part of the portion corresponding to the pad 46 of the jaw 27 at any portion of the part opposed to the pad 46. The first coating 51 is provided in the range of, for example, a length of ⅛ of the wavelength of the ultrasonic vibration (vibration) from the distal node position 37A of the vibration transmission member 23 toward the distal direction C1 side of the vibration transmission member 23. That is, in FIG. 4, the longitudinal direction C of the vibration transmission member 23 may be set so that length a of the first coating 51:length b of the second coating 52 is 1:1. In general, it is considered that the range of, for example, a length of ⅛ of the wavelength of ultrasonic vibration (vibration) from the distal end of the vibration transmission member 23 is a size sufficient to treat the tissue by the energy of ultrasonic vibration. In FIG. 4, the ratio of a:b is set under more preferable conditions described below.

From a standpoint of preventing the coating from peeling off, it is more preferable that the second coating 52 is provided in the range of, for example, a length of 1/16 of the wavelength of the ultrasonic vibration (vibration) from the distal end of the vibration transmission member 23. That is, in the range of the length of 1/16 of the wavelength of the ultrasonic vibration (vibration) from the distal end (distal antinode position 38A) of the vibration transmission member 23, a kinetic energy by vibration particularly increases, and it is desirable to provide the second coating 52 having a small thickness on this position. On the other hand, in this case, the first coating 51 is desirably provided in the range of, for example, a length of 3/16 of the wavelength of the ultrasonic vibration (vibration) from the distal node position 37A of the vibration transmission member 23 toward the distal direction C1 side of the vibration transmission member 23. In this case, sufficient thickness is ensured in the first coating 51, and sufficient insulation properties and heat insulation properties are exhibited at the portion corresponding to the first coating 51. Thus, in this preferred example (FIG. 4), length a of the first coating 51:length b of the second coating 52 is approximately 3:1. Even if the first coating 51 extends to the proximal end side of the vibration transmission member 23 relative to the distal node position 37A for manufacturing expediency, any effects are minimal and present no problems.

In the hand piece 12 not configured to seal the liquid by the supporting section 25 at the distal node position 37A, it is rather preferable to form a coating from the distal node position 37A to the proximal end side of the vibration transmission member 23. According to this configuration, even if blood from the treatment and conductive liquids such as a physiological saline solution enter inside the sheath 24, leakage of electricity can be effectively prevented by the coatings.

As shown in FIG. 1, the power source unit 13 includes the ultrasonic current supply section 36 (ultrasonic energy supply section), the high-frequency current supply section 53 (high-frequency energy supply section) and a control section 54 that controls them. The control section 54 can control supply of an ultrasonic wave generation current from the ultrasonic current supply section 36 and supply of a high-frequency current from the high-frequency current supply section 53. When an operator operates the operation button 18, an electrical signal is transmitted to the control section 54, and an input of an energy operation is detected. Accordingly, the control section 54 supplies an ultrasonic wave generation current from the ultrasonic current supply section 36 to the vibration generation section 22, and supplies a high-frequency current from the high-frequency current supply section 53 to the end effector 28.

A plurality of operation buttons 18 include a first operation button 18A corresponding to a coagulation mode, and a second operation button 18B corresponding to a coagulation/incision mode. For example, when the operator operates the first operation button 18A, under the control of the control section 54, ultrasonic energy and high-frequency energy suitable for coagulation of the living tissue are output from the end effector 28. When the operator operates the second operation button 18B, under the control of the control section 54, ultrasonic energy and high-frequency energy suitable for coagulation and incision of the living tissue are output from the end effector 28.

The process of manufacturing the first coating 51 and the second coating 52 is described. The first coating 51 and the second coating 52 are formed by performing film formation multiple times with coating materials (resin) on the vibration transmission member 23. For the film forming process, various processes may be used, including application (spray application and dipping), thermal spraying, molding, vacuum evaporation coating, and the like. The number of film formation times is different for the first coating 51 and the second coating 52, and because of the difference in the number of film formation times, the thicknesses are different. That is, the first coating 51 is formed by performing film formation more times than that of the second coating 52.

Next, an operation of the medical device of the present embodiment will be described with reference to FIG. 4, etc.

In the treatment, the operator operates the handle 17 to hold the living tissue between the vibration transmission member 23 and the jaw 27. The operator further operates the operation buttons 18 to apply energy to the living tissue held. When the second operation button 18B corresponding to the coagulation/incision mode is operated, the vibration transmission member 23 makes ultrasonic vibration, and applies a thermal energy (ultrasonic energy) of frictional motion to the living tissue. Simultaneously, a high-frequency current flows into the living tissue between the vibration transmission member 23 serving as a bipolar electrode and the jaw 27, and high-frequency energy can be applied to the body tissue. By these two types of energies, it is possible to coagulate and incise the living tissue.

The operator operates the first operation button 18A with the living tissue being held between the vibration transmission member 23 and the jaw 27 and thereby the high-frequency current flows to the living tissue held by the end effector 28 and the high-frequency energy can be applied to the living tissue. Thereby, it is also possible to only coagulate the living tissue.

Meanwhile, if the coagulation/incision treatment and the coagulation treatment are applied to the living tissue (treatment target) for a long period of time, the temperature of the end effector 28 may become high, for example, exceeding 200° C. In the present embodiment, the first coating 51 and the second coating 52 of the coating portion 31 are formed on the vibration transmission member 23. Thus, at the distal node position 37A side in which the kinetic energy by the ultrasonic vibration is relatively small, the vibration transmission member 23 can be coated with the first coating 51 having a sufficient thickness. Even if the vicinity of the distal node position 37A of the vibration transmission member 23 is accidentally brought into contact with the surrounding tissue, heat insulation properties can be exhibited at this portion, and thermal invasion to the surrounding tissue can be prevented. In this portion, moreover, the electrical insulation can be ensured, and leakage of the high-frequency energy (high-frequency current) to the surrounding tissue can be prevented.

At the distal end (distal antinode position 38A) of the vibration transmission member 23 in which the kinetic energy by the ultrasonic vibration is relatively large, the vibration transmission member 23 can be coated with the second coating 52 having a small thickness. Thus, rigidity of the second coating 52 can be relatively lowered, and the second coating 52 can follow the vibration transmission member 23 making ultrasonic vibration. The strength of the second coating 52 against peeling off can be thereby increased. Even when the back surface 44, which is the back side of the treatment surface 43, is brought into contact with the surrounding tissue at the vicinity of the distal end of the vibration transmission member 23, heat insulation properties are exhibited at this portion, and it is possible to prevent thermal invasion to the surrounding tissue and ensure the strength of the coating itself against ultrasonic driving. In this portion, moreover, the electrical insulation can be ensured, and leakage of high-frequency energy (high-frequency current) into the surrounding tissue can be prevented.

According to the first embodiment, the medical device 11 includes: a vibration transmission member 23 that comprises a node position 37 of vibration and an area 42 including the node position and a portion at a distal end side relative to the node position, and to which the vibration is transmitted; a first coating 51 that covers a side of the node position 37 of the area; and a second coating 52 that covers a distal end side relative to the first coating 51 of the area 42 and has a thickness smaller than that of the first coating.

In general, linear expansion coefficients are significantly different in the vibration transmission member 23 made of a metal and the coating made of a resin. When a shock (thermal shock) formed from the kinetic energy by vibration and the heat is transmitted to the vibration transmission member 23 and the coating having significantly different linear expansion coefficients, the coating is easily peeled off at the distal end side of the vibration transmission member 23 in which the kinetic energy is large. According to the above-described configuration, the thickness of the second coating 52 is smaller at the distal end side of the vibration transmission member 23, and thus rigidity and mass of the second coating 52 can be small. In this manner, the second coating 52 can follow the vibration of the vibration transmission member 23, and the strength of the second coating 52 against peeling off can be increased at the vicinity of the distal end of the vibration transmission member 23. Thus, durability can be improved, and it is possible to provide a medical device that is less invasive (thermal invasion, invasion due to electrical leakage) to the surrounding tissues at the treatment target area. Since the thickness of the coating can be small at the vicinity of the distal end of the vibration transmission member 23, a load of the vibration applied to the supply source at the time of vibration can be reduced.

The node position 37 is a node position located at the most distal end side of the vibration transmission member 23. According to this configuration, it is possible to provide a coating having strength against the coating peeling off at the distal end side of the vibration transmission member 23 that is likely brought into contact with the surrounding tissues accidentally during treatment, and it is possible to provide a medical device 11 less invasive to the tissues near the treatment area.

The medical device 11 includes a clamp member movable between the proximal position proximal to the vibration transmission member 23 and the spaced position spaced apart from the vibration transmission member 23 and having a pad 46 that is brought into contact with the vibration transmission member 23. The coating 52 is provided on a part corresponding to the pad 46 of the area 42. According to this configuration, the second coating 52, not the first coating 51, is disposed on the part corresponding to the pad 46 to thereby prevent the coating from being peeled off. It is thereby possible to provide a medical device that is less invasive to the surrounding tissues in the treatment area.

The second coating 52 is provided in the range of a length of ⅛ of the wavelength of the vibration from the distal end of the vibration transmission member 23. According to this configuration, in the range of ⅛ of the wavelength from the distal end of the vibration transmission member 23 where the kinetic energy by vibration is relatively large, the vibration transmission member 23 can be coated with the second coating 52 having a small thickness. It is thereby possible to further reduce the possibility that the coating is peeled off in the range of ⅛ of the wavelength from the distal end. Thus, it is possible to provide a medical device that is less invasive to the surrounding tissues in the treatment area.

The second coating 52 is provided in the range of a length of 1/16 of the wavelength of the vibration from the distal end of the vibration transmission member 23. According to this configuration, in the range of 1/16 of the wavelength from the distal end of the vibration transmission member 23 where the kinetic energy by vibration is the largest, the vibration transmission member 23 can be coated with the second coating 52 having a small thickness. Furthermore, in the range of 3/16 of the wavelength from the node position 37 side, the vibration transmission member 23 can be coated with the first coating 51 having a large thickness. It is thus possible to further reduce the possibility that the coating is peeled off at this part, and minimize a portion on which the second coating having a small thickness is provided. In the range of 3/16 of the wavelength from the node position 37 side, heat insulation properties and electrical insulation properties which are natural functions of coatings can be sufficiently exhibited, and it is possible to provide the medical device 11 that is less invasive to the surrounding tissues in the treatment target area.

Second Embodiment

Figure 5:
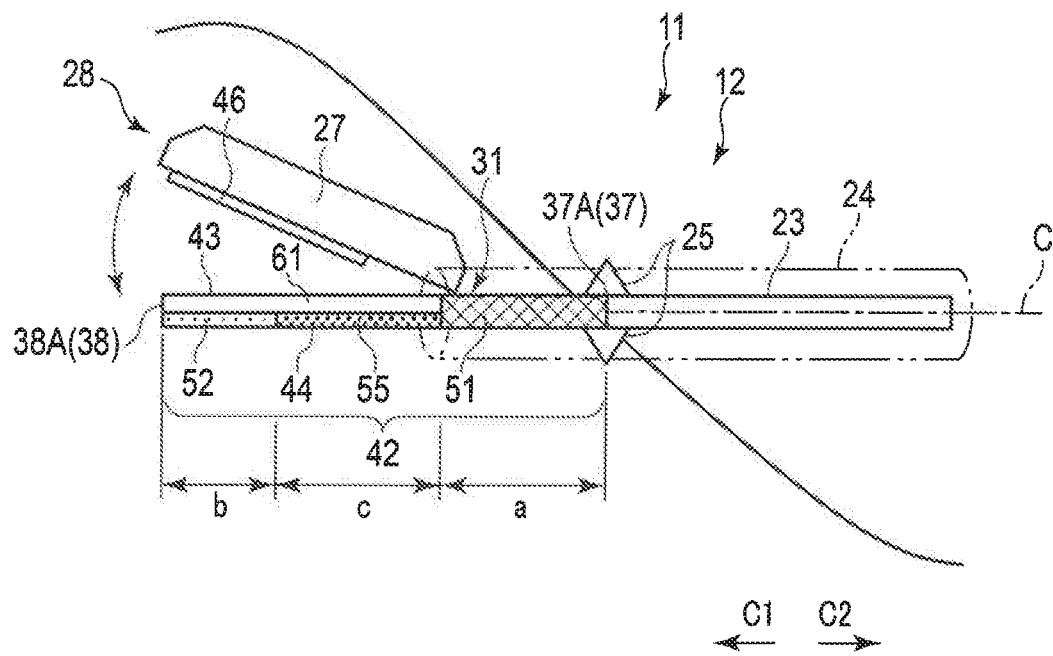
FIG. 5 is a side view of a medical device according to the second embodiment showing the vibration transmitting member, the jaw, the first to third coatings of the coating portion, and the waveform at the moment when the ultrasonic vibration transmitted to the vibration transmission member is at maximum amplitude.

A medical device according to the second embodiment will be described with reference to FIG. 5. The medical device 11 of the second embodiment differs from that of the first embodiment in that the coating portion 31 comprises a third coating 55 between the first coating 51 and the second coating 52, but is the same in the other respects. Therefore, mainly the parts different from those of the first embodiment will be explained, and illustrations or explanations of the parts identical to those of the first embodiment will be omitted.

The coating portion 31 includes the first coating 51 that covers the distal node position 37A (node position) side of the area 42 (treatment area) of the vibration transmission member 23, the second coating 52 that covers the distal direction C1 side of the vibration transmission member 23, and the third coating 55 provided between the first coating 51 and the second coating 52. The coating portion 31 is made of the resin (synthetic resin) having electrical insulation properties and heat insulation properties.

The first to third coatings 51, 52, and 55 are made of the same material but have different thicknesses. The second coating 52 has a thickness smaller than that of the third coating 55. The third coating 55 has a thickness smaller than that of the first coating 51. Specifically, in consideration of non-uniformity, the first coating 51 is formed to have a suitable thickness, for example, within the range of 100 to 200 µm, the third coating 55 is formed to have a suitable thickness, for example, within the range of 60 to 100 µm, and the second coating 52 is formed to have a suitable thickness, for example, within the range of 1 to 60 µm. More specifically, the thickness of the coating increases in a stepwise manner from the distal end (distal antinode position 38A) to the distal node position 37A of the vibration transmission member 23 (that is, the relationship of thicknesses is the thickness of the second coating 52<the thickness of the third coating 55<the thickness of the first coating 51). The second coating 52 and the third coating 55 are provided only on the back surface 44 of the vibration transmission member 23 at the position opposed to the jaw 27, and not provided on the treatment surface 43. On the other hand, the first coating 51 is disposed so as to cover the entire periphery of the vibration transmission member 23.

The second coating 52 is provided in the range of, for example, a length of $1/16$ of the wavelength of the ultrasonic vibration (vibration) from the distal end (distal antinode position 38A) of the vibration transmission member 23. In this case, the position where the second coating is provided is the position corresponding to the pad 46 of the jaw 27 and with which the pad 46 is brought into contact. The first coating 51 is provided in the range of, for example, a length of $1/16$ of the wavelength of the ultrasonic vibration (vibration) from the distal node position 37A of the vibration transmission member 23 toward the distal direction C1 side. The third coating 55 is provided in the range of $1/8$ of the wavelength of the ultrasonic vibration (vibration) between the first coating 51 and the second coating 52. That is, in FIG. 5, length a of the first coating 51:length b of the second coating 52:length c of the third coating 55 is approximately 1:1:2.

The process of manufacturing the first to third coatings 51, 52, and 55 will be described. The first to third coatings 51, 52, and 55 are formed by performing film formation multiple times with coating materials (resin) on the vibration transmission member 23. For the film forming method, various methods may be used, including application (spray application and dipping), thermal spraying, molding, vacuum evaporation coating, and the like. The number of film formation times is different in the first coating 51, the second coating 52, and the third coating 55, and because of the difference in the number of film formation times, the thicknesses are different. That is, the first coating 51 is formed by performing film formation more times than that of the third coating 55, and the third coating 55 is formed by performing film formation more times than that of the second coating 52.

According to this embodiment, in addition to the first coating 51 and the second coating 52, the third coating 55 is provided, and the thicknesses of coatings are set more precisely. Thus, a heat insulation effect and an electrical insulation effect which are natural functions of coatings are exhibited while preventing the coatings from being peeled off.

According to the second embodiment, the medical device 11 includes the third coating 55 provided between the first coating 51 and the second coating 52 of the area 42, and the third coating 55 has a thickness smaller than that of the first coating 51 and larger than that of the second coating 52.

According to this configuration, the second coating 52 having the smallest thickness is provided on the most distal end side of the vibration transmission member 23, the first coating 51 having the largest thickness is provided on the distal node position 37A of the vibration transmission member 23, and the third coating 55 having the middle thickness is provided on an intermediate position thereof. Thus, the coating thickness can be set smallest at the distal end side of the vibration transmission member 23 where the kinetic energy by vibration is the largest, and it is possible to prevent the coating from being peeled off at this portion. The kinetic energy by vibration is mid-level at the intermediate position, and the thickness of coating at the intermediate position can be set to be mid-level. Thus, the coating functions can be exhibited while preventing the coating from being peeled off at the intermediate position. Thus, it is possible to keep a balance between prevention of peeling off of the coatings and functional maintenance of the coatings. The kinetic energy by vibration is smaller at the distal node position 37A side, and a coating having a sufficient thickness can be formed on this portion.

Third Embodiment

Figure 6:
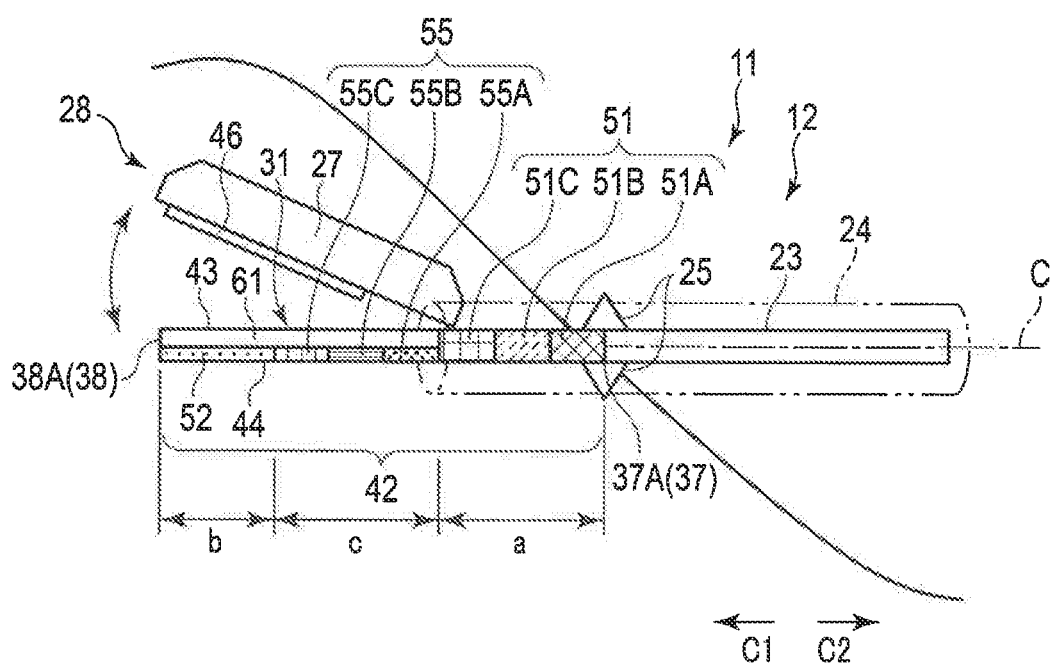
FIG. 6 is a side view of a medical device according to the third embodiment showing the vibration transmitting member, the jaw, the first to third coatings of the coating portion, and the waveform at the moment when the ultrasonic vibration transmitted to the vibration transmission member is at maximum amplitude.

A medical device according to the third embodiment will be described with reference to FIG. 6. The medical device 11 of the third embodiment differs from that of the first embodiment in that there are differences in the thickness in the first coating 51 and the thickness in the third coating 55, but is the same in the other respects. Therefore, mainly the parts different from those of the second embodiment will be explained, and illustrations or explanations of the parts identical to those of the second embodiment will be omitted.

The coating portion 31 includes the first coating 51 that covers the distal node position 37A (node position) side of the area 42 (treatment area) of the vibration transmission member 23, the second coating 52 that covers the distal side of the vibration transmission member 23, and the third coating 55 provided between the first coating 51 and the second coating 52. The coating portion 31 is made of the resin (synthetic resin) having electrical insulation properties and heat insulation properties. For the coating portion 31, resin materials such as PEEK may be used, but other types of resins may be used.

The first to third coatings 51, 52, and 55 are made of the same material but have different thicknesses. The second coating 52 has a thickness smaller than that of the third coating 55. The third coating 55 has a thickness smaller than that of the first coating 51. Specifically, in consideration of non-uniformity, the first coating 51 is formed to have a suitable thickness, for example, within the range of 100 to 200 μm, the third coating 55 is formed to have a suitable thickness, for example, within the range of 60 to 100 μm, and the second coating 52 is formed to have a suitable thickness, for example, within the range of 1 to 60 m. That is, the thickness of the coating gradually increases from the distal end (distal antinode position 38A) to the distal node position 37A (node position) of the vibration transmission member 23 (that is, the relationship of thicknesses is the thickness of the second coating 52<the thickness of the third coating 55<the thickness of the first coating 51). The second coating 52 and the third coating 55 are provided only on the back surface of the vibration transmission member 23 at the position opposed to the jaw 27, and not provided on the treatment surface 43. On the other hand, the first coating 51 covers the entire periphery of the vibration transmission member 23.

The first coating 51 is provided in the range of, for example, a length of ⅟₁₆ of the wavelength of the ultrasonic vibration (vibration) from the distal node position 37A of the vibration transmission member 23 toward the distal direction C1 side. The first coating 51 further includes three parts. The first coating 51 includes a first part 51A located closest to the distal node position 37A side, a second part 51B located on the distal end side of the vibration transmission member 23 relative to the first part 51A, and a third part 51C located on the most distal end side of the vibration transmission member 23 of the first coating 51. They have the relationship of "the thickness of the first part 51A>the thickness of the second part 51B>the thickness of the third part 51C". More specifically, in consideration of non-uniformity, the first part 51A is formed to have a suitable thickness, for example, within the range of 160 to 200 m, the second part 51B is formed to have a suitable thickness, for example, within the range of 130 to 160 μm, and the third part 51C is formed to have a suitable thickness, for example, within the range of 100 to 130 m. The first coating 51 is designed to have a thickness that increases toward the distal node position 37A. The thickness of the first coating 51 is the largest at the distal node position 37A.

The third coating 55 is provided in the range of ⅛ of the wavelength of the ultrasonic vibration (vibration) between the first coating 51 and the second coating 52. That is, in FIG. 6, length a of the first coating 51:length b of the second coating 52:length c of the third coating 55 is 1:1:2. The third coating 55 further includes three components. The third coating 55 includes a first component 55A located closest to the distal node position 37A side, a second component 55B located on the distal side of the vibration transmission member 23 relative to the first component 55A, and a third component 55C located on the most distal side of the vibration transmission member 23 of the third coating 55. They have the relationship of "the thickness of the first component 55A>the thickness of the second component 55B>the thickness of the third component 55C". That is, in consideration of non-uniformity, the first component 55A is formed to have a suitable thickness, for example, within the range of 90 to 100 Mm, the second component 55B is formed to have a suitable thickness, for example, within the range of 75 to 90 μm, and the third component 55C is formed to have a suitable thickness, for example, within the range of 60 to 75 m. The third coating 55 is designed to have a thickness that increases toward the distal node position 37A.

The second coating 52 and the third coating 55 are provided only on the back surface 44 of the vibration transmission member 23 at the position opposed to the jaw 27, and not provided on the treatment surface 43. On the other hand, the first coating 51 covers the entire periphery of the vibration transmission member 23.

The process of manufacturing the first to third coatings 51, 52, and 55 will be described. The first to third coatings 51, 52, and 55 are formed by performing film formation multiple times with coating materials (resin) on the vibration transmission member 23. For the film forming method, various methods may be used, including application (spray application and dipping), thermal spraying, molding, vacuum evaporation coating, and the like. The number of film formation times is different in the first coating 51, the second coating 52, and the third coating 55, and because of the difference in the number of film formation times, the thicknesses are different. The number of film formation times is different in the first coating 51 and the third coating 55, and because of the difference in the number of film formation times, the thicknesses of the first coating 51 and the third coating 55 are different.

That is, the first coating 51 is formed by performing film formation more times than that of the third coating 55, and the third coating 55 is formed by performing film formation more times than that of the second coating 52. That is, in the first coating 51, the first part 51A is formed by performing film formation more times than that of the second part 51B, and the second part 51B is formed by performing film formation more times than that of the third part 51C. Similarly, in the third coating 55, the first component 55A is formed by performing film formation more times than that of the second component 55B, and the second component 55B is formed by performing film formation more times than that of the third component 55C.

According to this embodiment, because of the difference in the coating thicknesses in the first coating 51 and the third coating 55, the thicknesses of coatings can be set more precisely to conform to a distribution of actual kinetic energy (amplitude) in the vibration transmission member 23. Thus, a heat insulation effect and an electrical insulation effect which are natural functions of coatings are exhibited while preventing the coatings from being peeled off.

According to the third embodiment, the thickness of the third coating 55 increases toward the first coating 51. The thickness of the first coating 51 is the largest at the node position 37. In general, as described in the above embodiment, the kinetic energy by vibration increases toward the distal end side of the vibration transmission member 23. If the thickness of the coating is increased at the distal end side of the vibration transmission member 23, peeling likely occurs. According to these configurations, the first coating 51 and the third coating 55 have thicknesses that gradually increase toward the node position 37. Thereby, the coating can have a sufficient thickness near the node position 37 where the energy by vibration becomes small. Thus, it is possible to provide the medical device 11 that is less invasive to the treatment target area while preventing peeling off of the coating.

In this embodiment, the first coating 51 and the third coating 55 are divided into the three parts or components, but the division is only an example and they may be divided into a plurality of parts or components other than three. In the first coating 51 and the third coating 55, the thickness may be changed in a non-stepwise (gradation) manner. In this embodiment, the third coating 55 may be interpreted as part of the second coating 52. In case of this interpretation (modification), the second coating 52 includes a plurality of components having different thicknesses. The thickness of the second coating 52 increases toward the distal node position 37A.

Modification of First to Third Embodiments

A modification of the medical device 11 according to the first to third embodiments will be described with reference to FIG. 7. In the following, mainly the parts different from those of the above embodiments will be explained.

Figure 7:
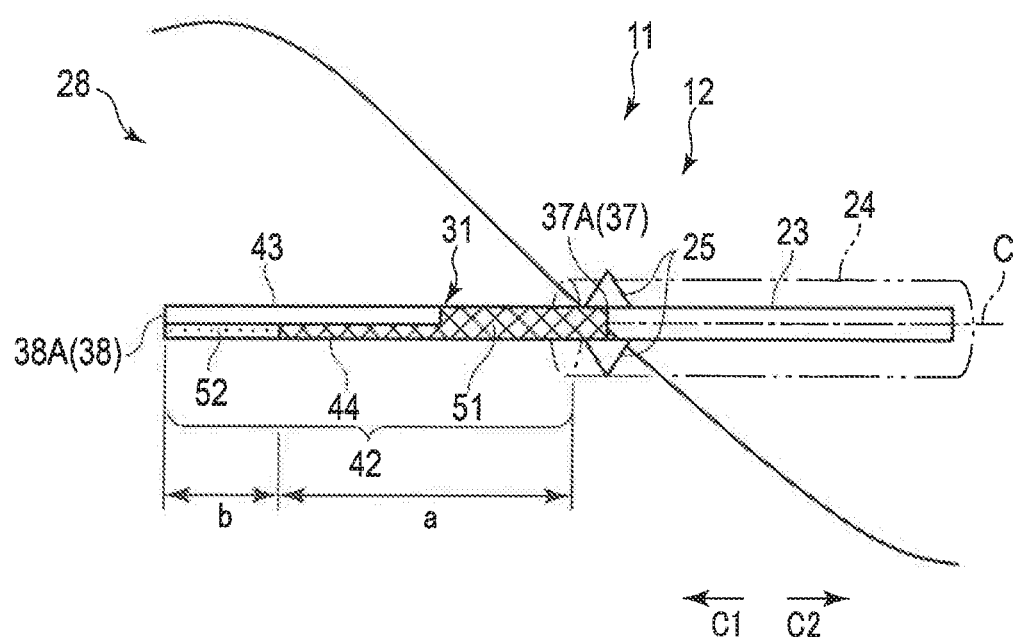
FIG. 7 is a side view of a medical device according to the modification of the first to third embodiments showing the vibration transmitting member, the jaw, the first to third coatings of the coating portion, and the waveform at the moment when the ultrasonic vibration transmitted to the vibration transmission member is at maximum amplitude.

The hand piece 12 of the medical device 11 of the above-described first to third embodiments may be formed without providing the jaw 27 (clamp member) as illustrated in FIG. 7. In this modification, the vibration transmission member 23 configures a so-called monopolar electrode in treatment in which a high-frequency current (high-frequency energy) is supplied to the treatment target. The vibration transmission member 23 is the same as that described in each of the above embodiments in terms of performing ultrasonic treatment by applying vibration (ultrasonic vibration) transmitted from the vibration generation section 22 to the living tissue.

According to this modification, in the so-called monopolar medical device 11 (treatment tool), it is possible to provide a medical device less invasive to the surrounding living tissues in the treatment area while preventing the coating from being peeled off.

The present invention is not limited to the above-described embodiments, and can be modified as appropriate in practice without departing from the gist of the invention. In addition, one medical device may be configured by properly combining the medical devices of the above embodiments and modification.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical device comprising:
  a vibration transmission member that comprises a node position of vibration and an area from the node position to a distal end position of the vibration transmission member, and is configured to receive the vibration;
  a first coating that covers the vibration transmission member from the distal end position to a predetermined position at a proximal end side relative to the distal end position of the area, the first coating having a linear expansion coefficient different from that of the vibration transmission member; and
  a second coating that covers a proximal end side of the vibration transmission member relative to the predetermined position of the area,
  wherein:
  the first coating has a thickness smaller than that of the second coating,
  the area includes a treatment surface configured to treat living tissue, and
  the treatment surface is an exposed section that extends from the distal end position towards the node position and is not covered with the first coating or the second coating.

2. The medical device of claim 1, wherein the node position is a distal-most node position.

3. The medical device of claim 1, further comprising:
  a clamp member that includes a pad and is movable between:
    a proximity position proximal to the vibration transmission member such that the pad is brought into contact with the vibration transmission member, and
    a spaced position spaced apart from the vibration transmission member,
  wherein the first coating is provided on any portion of a part opposed to the pad.

4. The medical device of claim 3, wherein the vibration transmission member is configured to receive ultrasonic energy and high-frequency energy simultaneously, and
  the exposed section includes a part configured to be brought into contact with the pad when the clamp member is in the proximity position.

5. The medical device of claim 1, wherein the first coating is provided in a range of a length of ⅛ of a wavelength of the vibration from the distal end position.

6. The medical device of claim 1, wherein the first coating is provided in a range of a length of 1/16 of a wavelength of the vibration from the distal end position.

7. The medical device of claim 1, wherein the first coating is made of a material having at least one property of a thermal conductivity lower than that of the vibration transmission member and an electronic resistance higher than that of the vibration transmission member.

8. The medical device of claim 1, further comprising:
  a third coating provided between the first coating and the second coating of the area,
  wherein the third coating has a thickness smaller than that of the second coating and larger than that of the first coating.

9. The medical device of claim 8, wherein the thickness of the third coating increases toward the second coating.

10. The medical device of claim 1, wherein the thickness of the second coating increases toward the node position.

11. The medical device of claim 1, wherein the thickness of the first coating increases toward the node position.

12. The medical device of claim 1, further comprising:
  a clamp member,
  wherein the treatment surface faces the clamp member.

13. The medical device of claim 12,
  wherein an entire periphery of a portion of the vibration transmission member not opposed to the clamp member is covered by the second coating.

14. The medical device of claim 12,
  wherein high-frequency energy is configured to flow between the exposed section and the clamp member.

15. The medical device of claim 1, wherein:
  the first coating terminates at the predetermined position, and
  the second coating does not cover the vibration transmission member between the distal end position and the predetermined position.

16. The medical device of claim 1,
  wherein the exposed section overlaps the first coating and/or the second coating in a direction orthogonal to an axial direction of the vibration transmission member.

17. The medical device of claim 1, wherein:
the second coating has electrical insulation properties, and
the second coating covers the node position.

\* \* \* \* \*